US010869701B2

(12) United States Patent
Van Dyke et al.

(10) Patent No.: US 10,869,701 B2
(45) Date of Patent: Dec. 22, 2020

(54) JOINT COMPRESSION INSTRUMENTATION AND METHODS

(71) Applicant: Biomet Manufacturing, LLC, Warsaw, IN (US)

(72) Inventors: William Scott Van Dyke, Warsaw, IN (US); Frank A Liporace, Englewood Cliffs, NJ (US); Dan Dziadosz, Tampa, FL (US); Jordan Grossman, Warsaw, IN (US); Jordi Asuncion Marquez, Warsaw, IN (US); David Thordarson, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 20 days.

(21) Appl. No.: 15/851,943

(22) Filed: Dec. 22, 2017

(65) Prior Publication Data

US 2018/0177537 A1 Jun. 28, 2018

Related U.S. Application Data

(60) Provisional application No. 62/439,545, filed on Dec. 28, 2016.

(51) Int. Cl.
*A61B 17/72* (2006.01)
*A61B 17/86* (2006.01)
*A61B 17/88* (2006.01)
*A61B 17/00* (2006.01)

(52) U.S. Cl.
CPC ...... *A61B 17/7225* (2013.01); *A61B 17/7291* (2013.01); *A61B 17/8665* (2013.01); *A61B 17/8866* (2013.01); *A61B 17/7233* (2013.01); *A61B 17/8872* (2013.01); *A61B 2017/00991* (2013.01)

(58) Field of Classification Search
CPC ............................................ A61B 17/72–7291
See application file for complete search history.

(56) References Cited

U.S. PATENT DOCUMENTS

| | | | |
|---|---|---|---|
| 2002/0072748 A1 | 6/2002 | Robioneck | |
| 2006/0064164 A1* | 3/2006 | Thelen | A61B 17/164 623/16.11 |
| 2008/0183171 A1 | 7/2008 | Elghazaly et al. | |
| 2012/0197255 A1* | 8/2012 | Elghazaly | A61B 17/725 606/64 |

(Continued)

FOREIGN PATENT DOCUMENTS

| | | |
|---|---|---|
| CN | 110352041 A | 10/2019 |
| WO | 2018125779 A1 | 7/2018 |

OTHER PUBLICATIONS

"International Application Serial No. PCT US2017 068091, Invitation to Pay Additional Fees and Partial Search Report dated Mar. 12, 2018", 14 pgs.

(Continued)

*Primary Examiner* — Nicholas J Plionis
(74) *Attorney, Agent, or Firm* — Schwegman Lundberg & Woessner, P.A.

(57) ABSTRACT

Various intramedullary implants, instruments, and methods are disclosed herein. In an example, a compression instrument is used to provide internal compression of bones adjoining a joint or bones spanning a fracture to cause compression of the joint or fracture.

13 Claims, 16 Drawing Sheets

(56) References Cited

U.S. PATENT DOCUMENTS

2012/0209268 A1    8/2012 Overes
2012/0330313 A1   12/2012 Grady et al.

OTHER PUBLICATIONS

Integra, "", Brochure—PANTA Arthrodesis Nail System Implantation and Removal Surgical Technique, 2014, 32 pgs.
Quill, George, et al., "", Brochure—Phoenix Ankle Arthrodesis Nail System—Featuring Dual Stage CoreLock Technology, Biomet Trauma, Warsaw Indiana, 2013, 40 pgs.
"International Application Serial No. PCT US2017 068091, International Search Report dated May 24, 2018", 6 pgs.
"International Application Serial No. PCT US2017 068091, Written Opinion dated May 24, 2018", 8 pgs.
"European Application Serial No. 17838106.7, Response to Communication pursuant to Rules 161(1) and 162 EPC filed Feb. 17, 2020", 15 pgs.

\* cited by examiner

JOINT COMPRESSION INSTRUMENTATION AND METHODS

CROSS-REFERENCE TO RELATED APPLICATIONS

This application is a non-provisional application that claims the benefit of the tiling date of U.S. Provisional Application Ser. No. 62/439,545, filed Dec. 28, 2016 the disclosure of which is hereby incorporated by reference in its entirety.

FIELD OF THE DISCLOSURE

The present disclosure relates to surgical implant systems, including implants, instruments, and methods for installing an implant. Specifically, the present disclosure relates to intramedullary devices, and instruments and methods for providing compression using the intramedullary devices.

BACKGROUND

Intramedullary implants are used in various contexts, including to repair fractures or to achieve joint fusion (i.e., arthrodesis). In the case of arthrodesis, it is frequently necessary to apply compression across one or more joints to bring the adjoining bones of the joint into apposition, and then fix the adjoining bones so that fusion can occur across the joint site. An intramedullary implant can be used to achieve fixation of adjoining bones of a joint after compression and secure the bones in position to allow fusion to occur. Yet, in a number of cases, compression of the joint structures occurs externally of the intramedullary device. As an example, U.S. Pat. No. 9,308,031 ("the '031 Patent") discloses a compression instrument that contacts the patient's foot externally and applies pressure to the patient's calcaneus externally to bring the calcaneal bone into apposition against the patient's talus.

The present disclosure provides intramedullary implants, instruments, and methods that allow for internal compression across various joints, as described in more detail below.

SUMMARY

To better illustrate the system disclosed herein, a non-limiting list of examples is provided here:

Example 1 includes an implant system comprising an intramedullary implant comprising an internal bore and a first slot, a first fixation member having a shaft, and a compression instrument. The compression instrument can have a shaft with a first section shaped to engage the shaft of the first fixation member, wherein the shaft of the compression instrument is movable within the internal bore of the implant, with the first fixation member in the first slot, so that the first section of the shaft engages the shaft of the first fixation member and moves the first fixation member from a first position in the first slot to a second different position.

In Example 2, the implant system of Example 1 can optionally include the shaft of the compression instrument having a threaded body, the compression instrument further comprising a threaded nut rotatably engaged to the threaded body.

In Example 3, rotation of the threaded nut relative to the threaded body can cause the shaft of the compression instrument to move longitudinally relative to the threaded nut from a first position to a second different position. In other examples, rotation of the threaded nut relative to the threaded body causes the shaft of the compression instrument to move longitudinally, but not rotationally.

In Example 4, the implant system of any one of or any combination of Examples 1-3 can optionally include an anti-rotation member disposed about the shaft of the compression instrument and configured to rotationally lock the shaft relative to the anti-rotation member.

In Example 5, the implant system of any one of or any combination of Examples 1-4 can optionally include the intramedullary implant further comprising a second slot located distally of the first slot, and a second fixation member having a shaft.

In Example 6, the implant system of Example 5 can further comprise a telescoping clamp having a body defining a first area shaped to engage the shaft of the second fixation member, wherein the telescoping clamp is disposable in the internal bore of the implant adjacent the second slot and is movable within the internal bore, with the second fixation member in the second slot, so that the first area of the body of the telescoping clamp engages the shaft of the second fixation member and moves the second fixation member from a first position in the second slot to a second different position.

In Example 7, the telescoping clamp of Example 6 comprises a threaded portion that is rotatable relative to the body, and the internal bore of the implant is threaded, such that rotation of the threaded portion of the telescoping clamp relative to the body within the threaded internal bore causes the telescoping clamp to move from a first position to a second position within the threaded internal bore.

In Example 8, the implant system of any one of or any combination of Examples 1-7 can optionally further comprise a jig nose having a shaft and a body and an internal bore through the shaft and the body, wherein a portion of the jig nose is engageable with the intramedullary implant, and the shaft of the compression instrument is insertable into the internal bore of the jig nose.

Example 9 includes an ankle arthrodesis implant comprising an elongate shaft sized and shaped to be implanted in an intramedullary canal of a tibia of a patient, the elongate shaft having an internal bore, a first angled opening through the shaft, the first angled opening defining a first axis that extends through the tibia and into a talus bone of the patient across a tibio-talar joint when the intramedullary nail is implanted, a first elongate slot through the shaft, the first elongate slot defining a second axis that extends into the patient's talus when the intramedullary nail is implanted, the first elongate slot being configured to allow a first fixation member to translate axially relative to the shaft within the first slot from a first position to a second different position to compress a tibio-talar joint, a second elongate slot through the shaft, the second elongate slot defining a third axis that extends into the patient's calcaneus when the intramedullary nail is implanted, the second elongate slot being configured to allow a second fixation member to translate axially relative to the shaft within the second slot from a first position to a second different position to compress a subtalar joint, and a second angled opening through the shaft, the second angled opening defining a third axis that extends into a calcaneus bone of the patient when the intramedullary nail is implanted.

In Example 10, the internal bore of the ankle arthrodesis implant of Example 9 can be threaded.

Example 11 includes an implant system comprising the ankle arthrodesis implant of any one of or any combination of Examples 9-10 and first, second, third, and fourth fixation members each defining a diameter, wherein the first and second elongate slots each has a length that is anywhere between about 125-500% of the diameter of the second and third fixation members, and a width that is substantially equal to or under 120% of the diameter of the second and third fixation members, respectively.

In Example 12, the implant system of Example 11 can further comprise a telescoping clamp having a body defining a first area shaped to engage the first fixation member, wherein the telescoping clamp is disposable in the internal bore of the implant adjacent the first slot and is movable within the internal bore, with the first fixation member in the first slot, so that the first area of the body of the telescoping clamp engages the shaft of the first fixation member and moves the first fixation member from a first position in the first slot to a second different position.

In Example 13, the implant or implant system of any one of or any combination of Examples 9-12 can further comprise a third angled opening through the shaft, the third angled opening defining a fourth axis that extends through the calcaneus and into a talus bone of the patient across the subtalar joint when the intramedullary nail is implanted.

Example 14 includes a method of implanting an intramedullary implant comprising implanting an intramedullary implant into an intramedullary canal of a bone, the intramedullary implant having a shaft and an internal bore, inserting a first fixation member into a first elongate slot extending through the shaft and into bone, inserting a second fixation member into a second elongate slot extending through the shaft and into bone, subsequently engaging the first fixation member internally within the internal bore with a first telescoping member to move the first fixation member within the first elongate slot from a first position to a second different position, and engaging the second fixation member internally within the internal bore with a second telescoping member to move the second fixation member within the second elongate slot from a first position to a second position.

In Example 15, the first telescoping member of Example 14 can be a telescoping clamp having a first area shaped to engage the first fixation member, and the second telescoping member is a shaft of a compression instrument.

In Example 16, in the method of any one of or any combination of Examples 14-15, the intramedullary canal is an intramedullary canal of a tibia, the first fixation member is inserted through the first elongate slot into a talus bone, and the second fixation member is inserted through the second elongate slot into a calcaneus bone, and wherein movement of the first fixation member causes compression of a tibio-talar joint, and movement of the second fixation member causes compression of subtalar joint.

In Example 17, the method of any one of or any combination of Examples 14-16 can optionally further comprise engaging the second fixation member internally within the internal bore with a shaft of a compression instrument.

In Example 18, the method of Example 17 can further comprise rotating a compression nut relative to the shaft of the compression instrument to move the shaft longitudinally against the second fixation member.

In Example 19, the method of Example 18 can further comprise inserting the shaft of the compression instrument into the internal bore of the intramedullary implant and moving the shaft against the second fixation member.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure in any manner.

DETAILED DESCRIPTION

In describing the examples of the invention(s) illustrated and to be described with respect to the drawings, specific terminology will be used for the sake of clarity. However, the invention(s) is not intended to be limited to any specific terms used herein, and it is to be understood that each specific term includes all technical equivalents.

As used herein, the following directional definitions apply. Anterior and posterior mean nearer the front or nearer the rear of the body, respectively; proximal and distal mean nearer to or further from the root of a structure, respectively; and medial and lateral mean nearer the sagittal plane or further from the sagittal plane, respectively. The sagittal plane is an imaginary vertical plane through the middle of the body or body structure that divides the body or body structure into right and left halves. In addition, the terms implant and prosthesis, and variations thereof, can be used interchangeably.

The present disclosure is directed to intramedullary implants and compression instruments that provide for compression of bone parts or bones adjoining a joint internally through the intramedullary implant. In this way, a simpler and more-effective compression technique can be carried out, which removes deficiencies associated with other compression techniques or methods.

Figure 1:
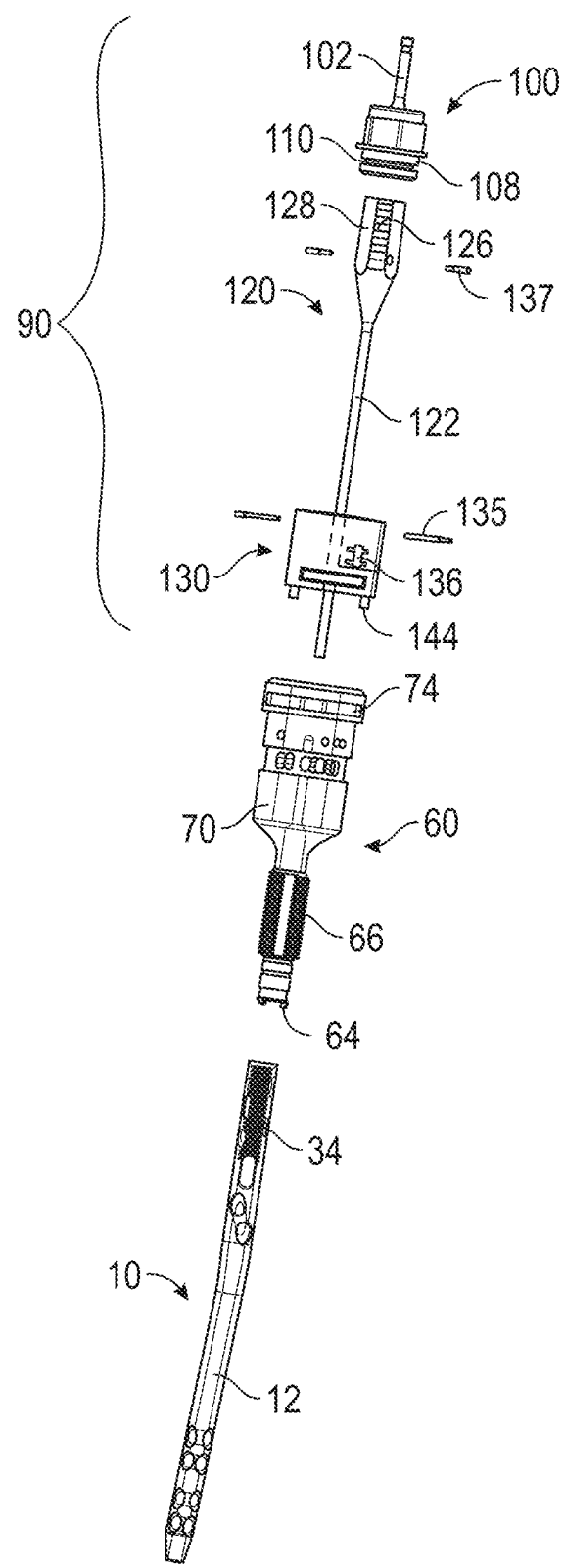
FIG. 1 is an exploded view of an intramedullary implant and a compression instrument usable with the intramedullary implant.

Referring to FIG. 1, an intramedullary implant 10 is shown in the form of an intramedullary nail (e.g., an IM ankle nail). FIG. 1 also illustrates a jig nose 60 and a compression instrument 90 attachable to jig nose 60 for applying compression across bone parts or bones adjoining a joint internally through implant 10. For the sake of convenience, the remainder of the disclosure shall refer to use of implant 10, jig nose 60, and compression instrument 90 to compress bones adjoining a joint together, although it is equally contemplated that such implants and instruments can instead be used to compress bone fragments or parts together (e.g., in the case of repairing a fracture).

Figure 9A:
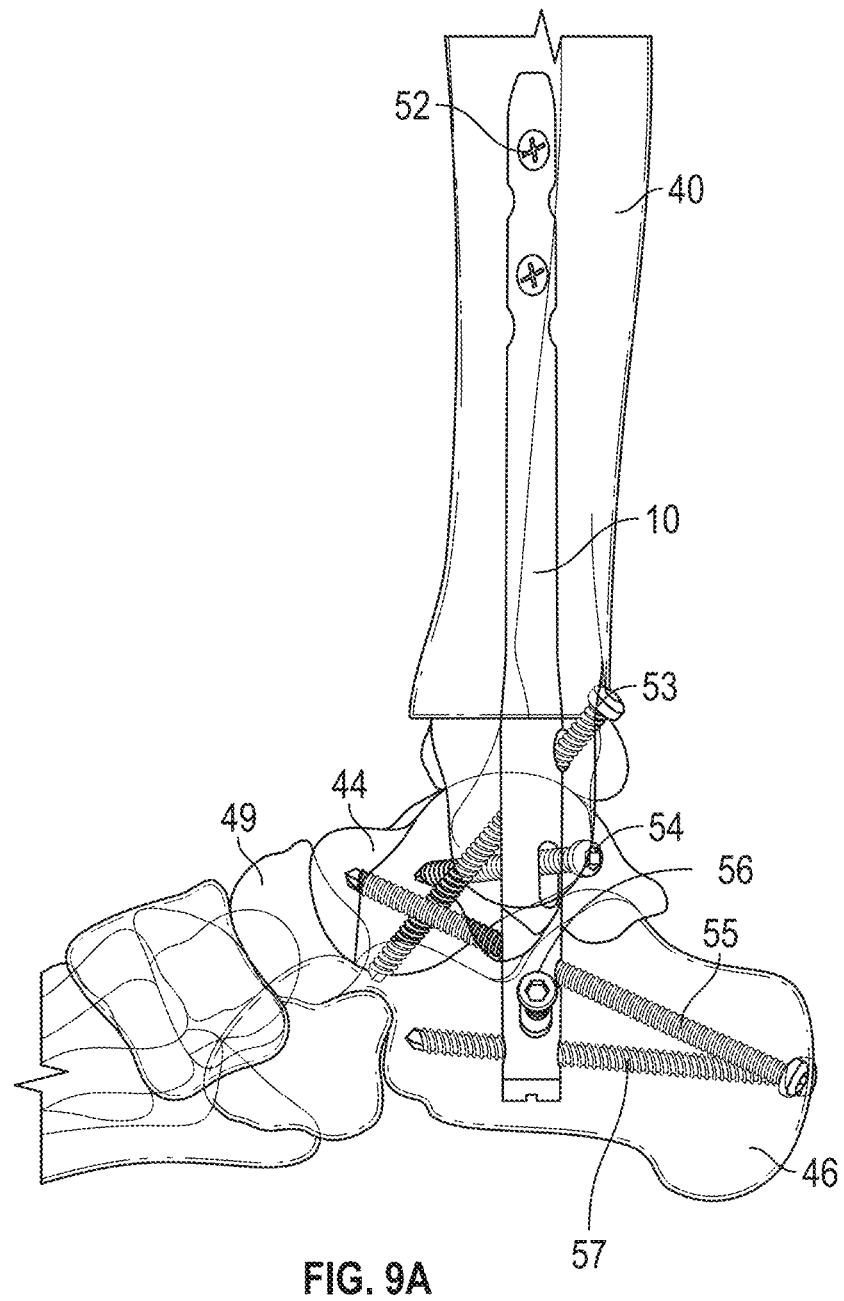
FIGS. 9A-C are various anatomical views of the intramedullary implant of FIG. 1 inserted through the ankle and into the tibia of a patient using a number of bone screws.
Figure 9B:
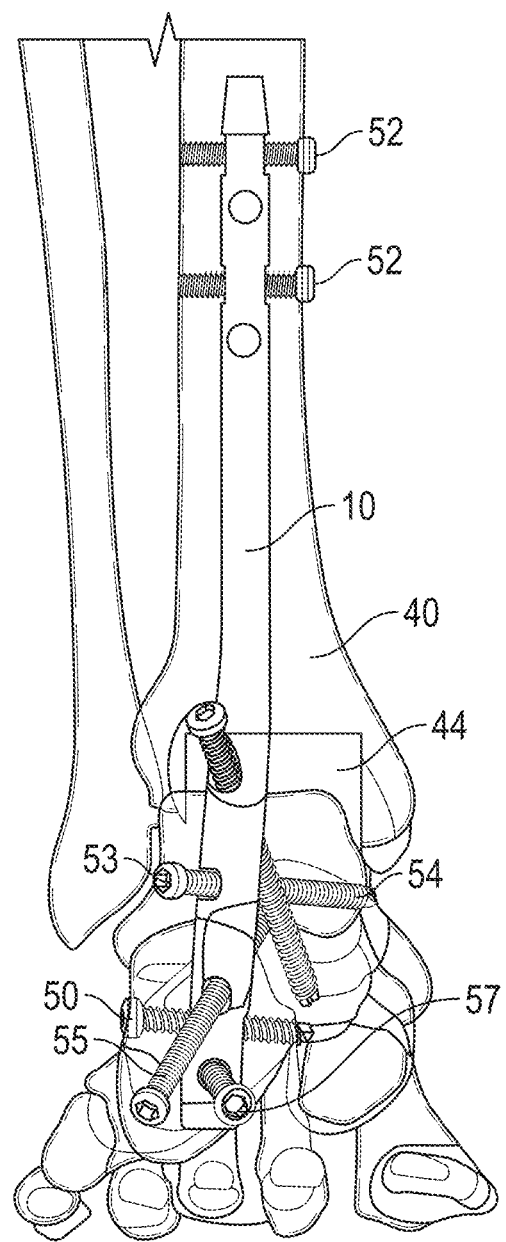
Figure 9C:
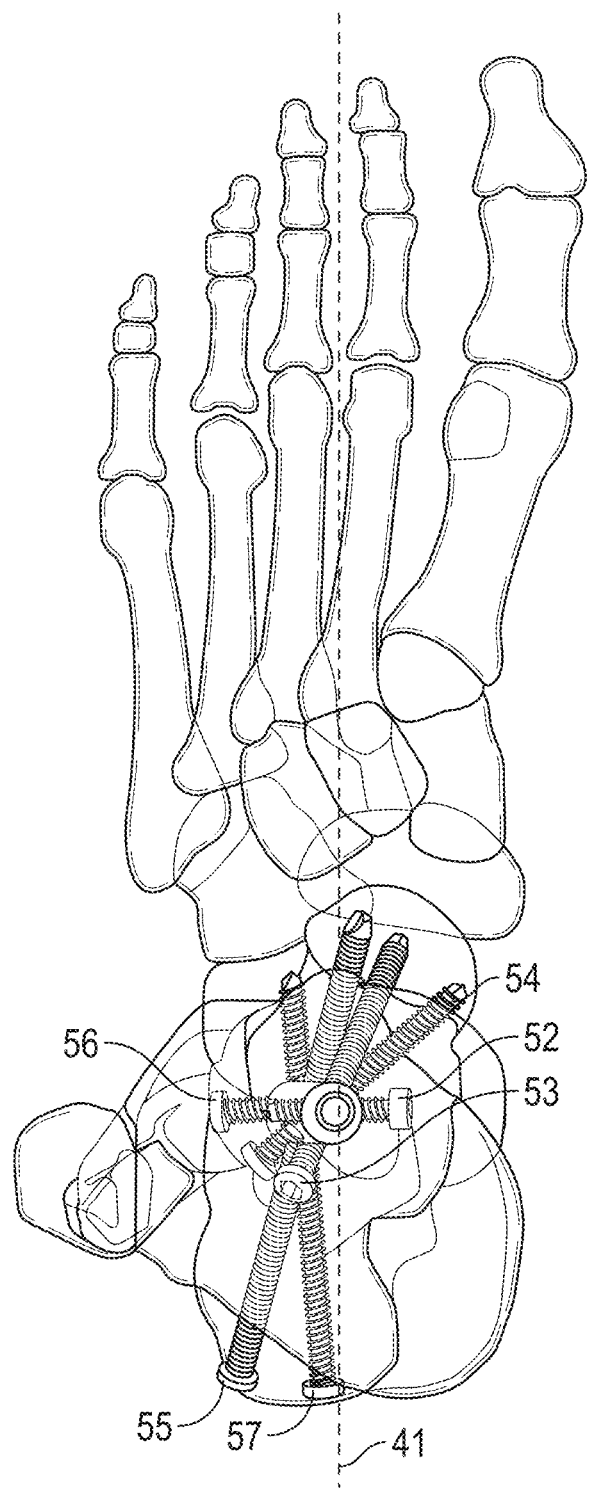

FIGS. 10A-D illustrate implant 10. Implant 10 can have a shaft 12 with a bend 11 between a proximal section of shaft 12 and a distal section of shaft 12. Bend 11 can be anywhere between about two degrees to about fifteen degrees (2-15°), in another example anywhere between about five degrees to about ten degrees (5-10°), or in yet another example about five degrees (5°). Thus, the proximal section of shaft 12 can define an axis 21 and the distal section of shaft 12 can define an axis 23, and the axes 21, 23 can intersect to form any of the aforementioned angles. Implant 10 can also include a set of distal openings 14, 16, 18, 20 for receiving bone screws 52, as shown in FIGS. 9A-C. Any of openings 14, 16, 18, 20 can be threaded or unthreaded, in any combination. Openings 14, 16, 18, 20 can also be arranged substantially perpendicular to axis 23, in an example, or any of openings 14, 16, 18, 20 can be a slot similar to first slot 24 described below.

Implant 10 can further include a first angled opening 22 through shaft 12 at the proximal section of shaft 12. In an example, opening 22 can be angled through shaft 12 proximally by between about thirty five degrees to about fifty degrees (35-50°), or alternatively about forty five degrees (45°) proximally relative to axis 21. Opening 22 can also be angled approximately anywhere between about twenty degrees to about thirty degrees (20-30°), in an example about twenty eight degrees (28°), medially relative to a sagittal plane 41 extending through the patient's ankle, as illustrated in FIG. 9C. As shown in FIGS. 9A-C, this can create a situation in which a bone screw 53 can be inserted downwardly through opening 22 and into a patient's tibia 40 and talus 44. In an example, screw 53 is approximately sixty two and a half millimeters (62.5 mm) in length and can extend into tibia 40 and talus 44 when inserted through opening 22. In another example, screw 53 can be of a different length and also extend into the patient's navicular 49—i.e., through tibia 40, talus 44, and into navicular 49. In an example, it can be said that an imaginary central axis of opening 22 can extend and/or project through tibia 40, talus 44, and navicular 49 (e.g., so that a certain size screw can extend into the foregoing bones, depending upon its length).

Implant 10 can include a first slot 24 that is elongated along axis 21. Slot 24 can have a width that is approximately the same as a bone screw 54 and a length that is greater than the width, in an example a length that is anywhere between about one-hundred and twenty five percent to four hundred percent (125-400%) of the diameter of bone screw 54. In another example, slot 24 can have a length that is approximately fourteen and three-quarter millimeters (14.75 mm) and a width that is approximately six millimeters (6 mm). The elongate length of slot 24 can allow bone screw 54 to move longitudinally within slot 24 by anywhere between about two millimeters to about ten millimeters (2-10 mm), in an example about seven millimeters (7 mm). Such movement of screw 54, as described in more detail below, can act to compress a patient's talus 44 against the patient's tibia 40. Further, as shown in FIG. 9C, a central axis of slot 24, as exemplified by the position of screw 54, can be angled medially relative to sagittal plane 41 by anywhere between about thirty degrees to about sixty degrees (30-60°), in an example by about fifty degrees (50°). This creates a situation in which screw 54 inserted through slot 24 extends along the same medial angle as slot 24.

Implant 10 can also have a second angled opening 26 extending through shaft 12, which is arranged proximally of slot 24. Opening 26 can be angled distally relative to axis 21 by anywhere between about twenty degrees to about thirty five degrees (20-35°), in an example about twenty five degrees (25°). Further, opening 26 can be angled medially relative to sagittal plane 41, as shown in FIG. 9C, by anywhere between about ten degrees to about twenty five degrees (10-25°), in an example about thirteen degrees (13°). As shown in FIGS. 9A-C, this can create a situation in which a screw 55 inserted through opening 26 can extend through a patient's calcaneus 46 and into the patient's talus 44. In an example, screw 55 can be anywhere between about thirty millimeters to about sixty millimeters (30-60 mm) in length, in a specific example about forty eight millimeters (48 mm).

Figure 10A:
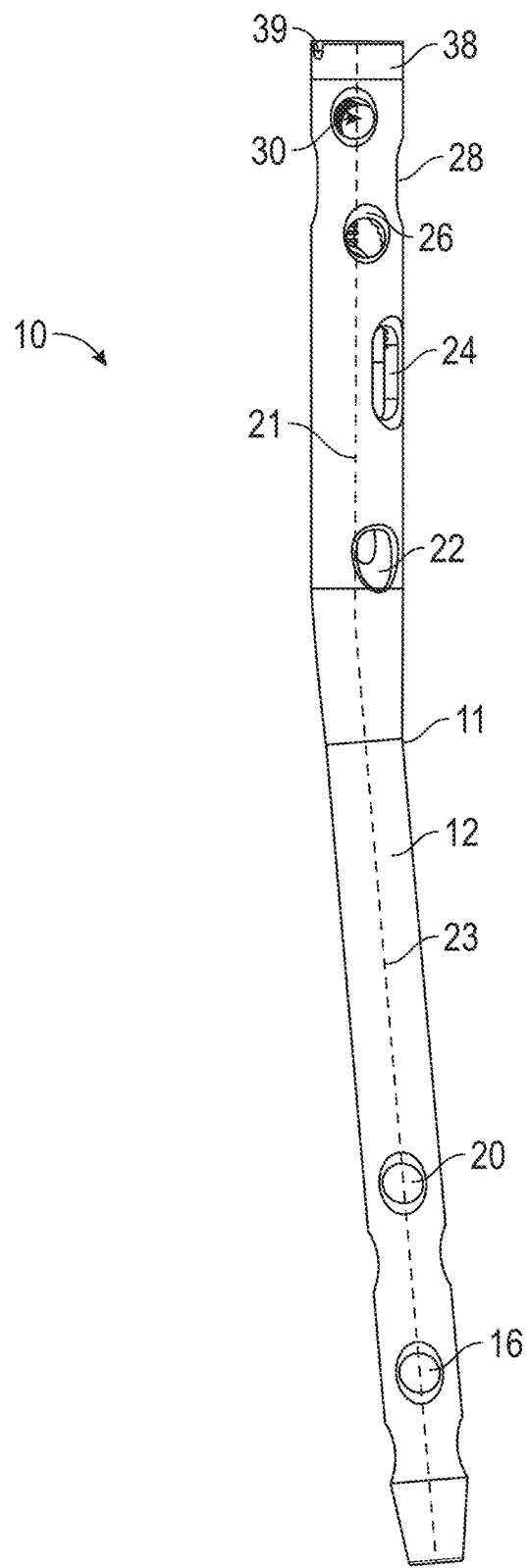
FIG. 10A is a side view of the intramedullary implant shown in FIG. 1.
Figure 10B:
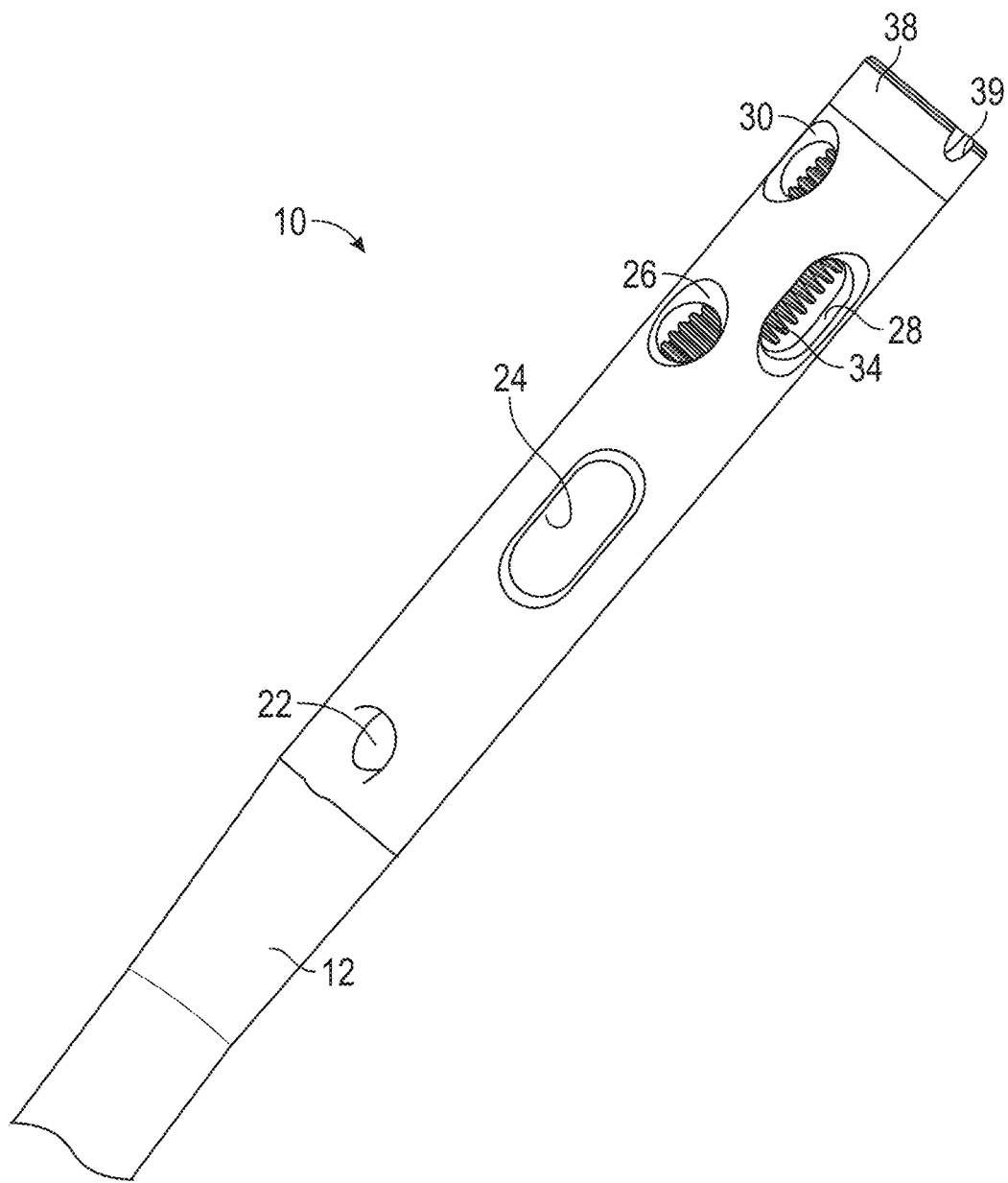
FIG. 10B is a close-up view of a proximal section of the intramedullary implant of FIG. 10A.

A second slot 28 can also be disposed through shaft 12 of implant 10, as shown in FIG. 10B. Slot 28 can have a width that is approximately the same as a bone screw 56 and a length that is greater than the width, in an example a length that is anywhere between about one-hundred and twenty five percent to four hundred percent (125-400%) of the diameter of bone screw 56. In another example, slot 28 can have a length that is approximately eleven and three-quarter millimeters (11.75 mm) and a width that is approximately six millimeters (6 mm). The elongate length of slot 28 can allow bone screw 56 to move longitudinally within slot 28 by anywhere between about two millimeters to about ten millimeters (2-10 mm), in an example about four millimeters (4 mm). Such movement of screw 56, as described in more detail below, can act to compress a patient's calcaneus 46 against the patient's talus 44. Further, as shown in FIG. 9C, a central axis of slot 28 can extend roughly perpendicular or alternatively transverse to sagittal plane 41 so that screw 56 can extend through calcaneus 46 in a medial-to-lateral direction. In an example, screw 56 can be anywhere between about fifteen millimeters to about twenty five millimeters (15-25 mm) in length, in a specific example about sixteen and a half to about twenty and a half millimeters (16.5-20.5 mm) in length.

Implant 10 can further include a final angled opening 30. Opening 30 can be angled distally relative to axis 21 by anywhere between about two degrees to about fifteen degrees (2-15°), in an example about five degrees (5°). In addition, opening 30 can be angled laterally relative to sagittal plane 41 by anywhere between about two degrees to about fifteen degrees (2-15°), in an example about five degrees (5°). As shown in FIGS. 9A-C, this can create a situation in which a screw 57 inserted into opening 30 extends upwards and laterally by the above angle amounts in the patient's calcaneus 46. In an example, screw 57 can be anywhere between about fifty millimeters to about ninety millimeters (50-90 mm) in length, in a specific example seventy five millimeters (75 mm) in length. In another example, screw 57 can be of a sufficient length to extend through calcaneus 46 and into a patient's cuboid across the calcaneus-cuboid joint.

Figure 10C:
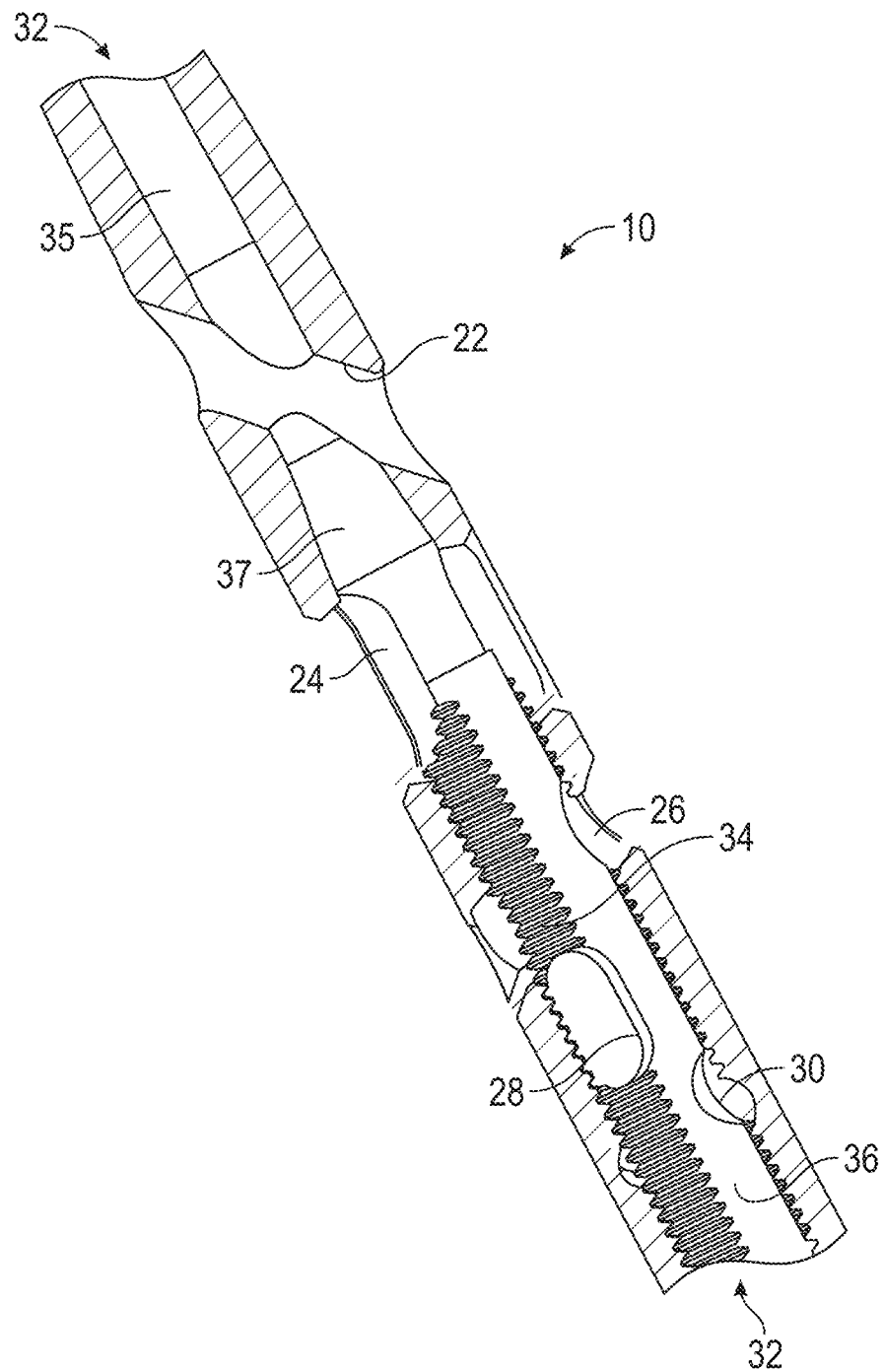
FIG. 10C is a cross-sectional view of FIG. 10B.
Figure 10D:
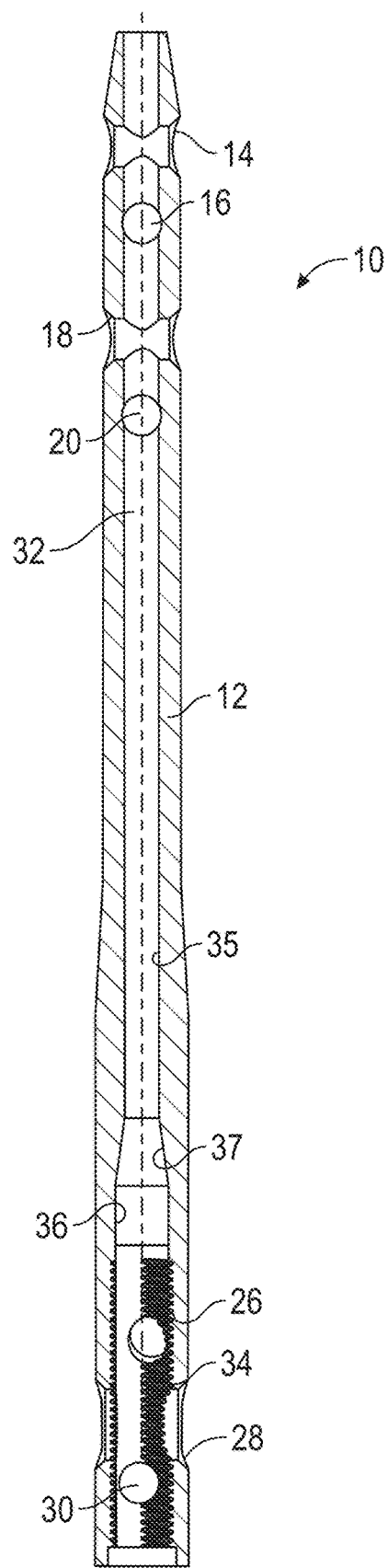
FIG. 10D is a cross-sectional view of the intramedullary implant of FIGS. 10A-C.

As shown in FIGS. 10C-D, implant 10 can also be hollow, such that a bore 32 extends through shaft 12. Bore 32 can define a first distal bore part 35 and a second proximal bore part 36, where the diameter of proximal bore part 36 can be greater than that of distal bore part 35. This difference in diameters can act to create a transition zone or taper 37 between bore parts 35, 36. Further, a portion or all of proximal bore part 36 can be threaded 34. In an example, threading 34 can extend from a proximal end of proximal bore part 36 and encompass part or all of the walls defining proximal bore part 36 along the extent of first slot 24. Likewise, threading 34 can extend along part or all of the walls defining proximal bore part 36 along the extent of second slot 28. As describe in more detail subsequently, such threading 34 can be used with CoreLock™ Technology, developed by Biomet, Inc.

Briefly, CoreLock™ Technology is exemplified in the '031 Patent discussed above, the disclosure of which is hereby incorporated by reference herein. By CoreLock™ Technology, Applicant is referring to any of the telescopic clamps, securing devices, locking devices, and/or compression devices disclosed in the '031 Patent, for example securing devices 200 (see e.g., FIG. 16), 700 (see e.g., FIGS. 25-26), and 900 (see e.g., FIGS. 34-35) and locking device 1030 (see e.g., FIGS. 44-44A) and compression device 1024 (see e.g., FIGS. 45-45A). It is to be understood that the aforementioned securing, locking, and compression devices of the '031 Patent can be used with implant 10 in ways that would be appreciated by a person of skill in the art, in varying combinations. Thus, implant 10 can have characteristics that make it suitable for use with such securing, locking, and compression devices. For example, a portion of bore 32—e.g., proximal bore part 36—can be keyed as is described with reference to, amongst other areas, FIGS. 47A-47B of the '031 Patent. As set forth in the '031 Patent, for example with reference to locking device 1030 and compression device 1024, a portion of longitudinal bore 1006 of IM implant 1002 can be keyed as at 1020, 1022 so as to key with second component 1078 of locking device 1030 and/or second component 1076 of compression device 1024. This creates a situation in which first components 1050, 1046 of the locking and compression devices 1030, 1024 can be rotated relative to second components 1078, 1076 and, by virtue of the threaded interaction between first components 1050, 1046 and the IM longitudinal bore 1006, locking and compression devices 1030, 1024 can be moved longitudinally relative to the IM implant. Such movement can cause screws associated with the respective securing, compression, or locking device to be secured, compressed in a particular direction within a slot of the IM implant, or locked, respectively. As described in more detail below, Applicant contemplates that such mechanisms can be used herein to lock and/or cause translation of any of screws 53-57 within openings 22, 26, 30 and slots 24, 28. Certain examples from the '031 Patent might be used for simplicity's sake, but it is to be understood that any of the securing, locking, and/or compression devices of the '031 Patent can be used with implant 10 and the instrumentation described herein.

It should also be noted that first components 1050, 1046 of locking and compression devices 1030, 1024 can further include generally similar features, and are also described in detail in U.S. Pat. No. 8,303,590 ("'590 Patent"), filed Jan. 26, 2007, the disclosure of which is hereby incorporated by reference herein. The use of the aforementioned securing, locking, and/or compression devices of the '031 Patent will, for the moment, be set aside but revisited in the disclosure below.

Turning to FIGS. 1 and 2A-C, a jig nose 60 is illustrated therein. Jig nose 60 can be attachable to implant 10, as shown in FIG. 1, via one or more protrusions 64 on a distal section of a shaft 62 of jig nose 60. Alternatively, one or more recesses can be used instead of protrusions. Jig nose 60 can have a body 70 with shaft 62 extending from body 70. Shaft 62 can have threaded sections 66 and substantially-flat sections 68. In an example, two to four or more threaded sections 66 can be included on shaft 62, as well as two to four or more substantially-flat sections 68. Threaded sections 66 can be curved along a cross-sectional direction of shaft 62 so that, collectively, threaded sections 66 can define a somewhat cylindrically-threaded shape. As described below, this is so that shall 62 can interact with a threaded portion of an externally-mounted compression nut, similar to compression nut 1124 of the '031 Patent. Thus, although jig nose 60 can be configured for internal compression as described below, jig nose 60 can also be used with externally-mounted compression instruments, such as compression nut 1124 of the '031 Patent, if needed (e.g., to augment internal compression).

Figure 2A:
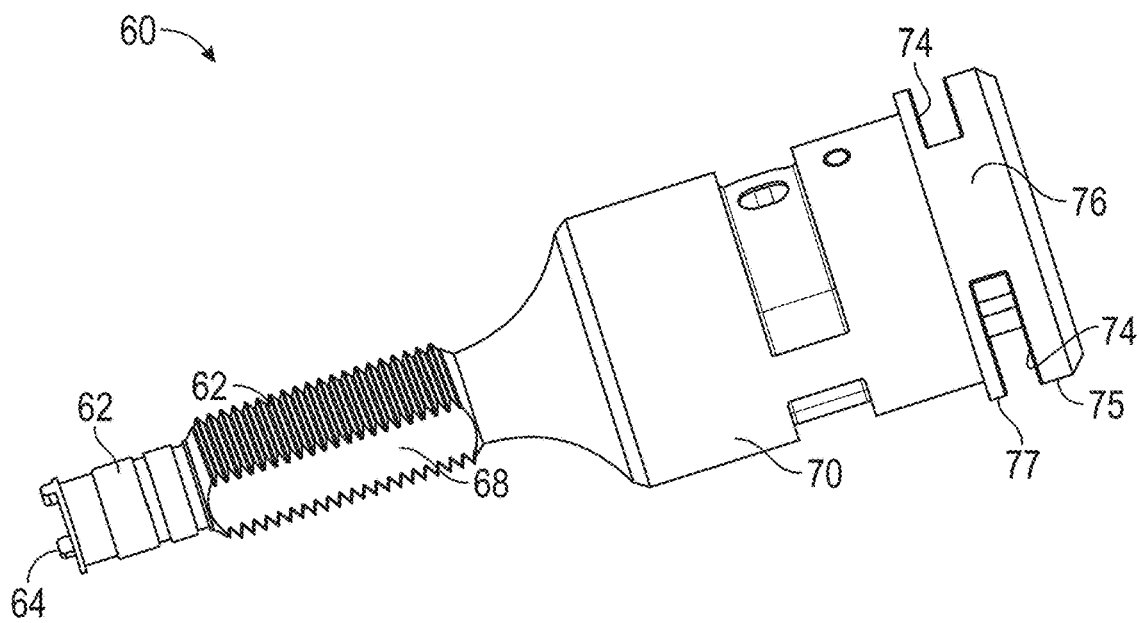
FIGS. 2A-C are several perspective views (FIGS. 2A-B) and a top view (FIG. 2C) of a jig nose of the compression instrument shown in FIG. 1.
Figure 2B:
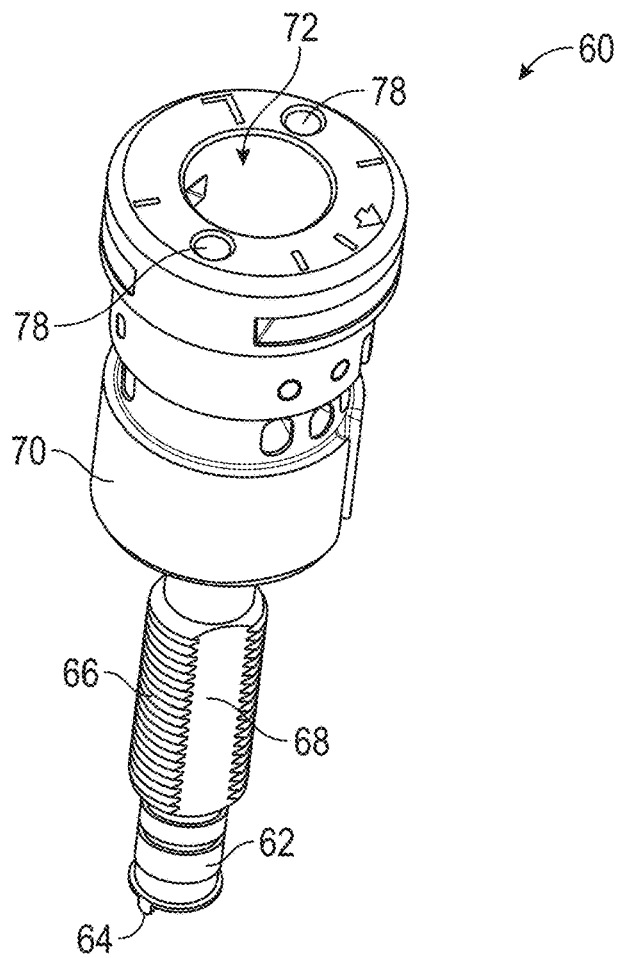
Figure 2C:
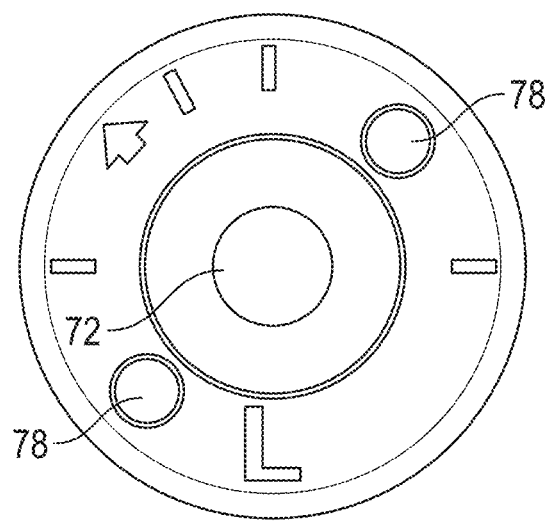

Jig nose 60 can also include a lumen 72 through body 70 and shaft 62, and openings or cutouts 74 in a proximal section of body 70. Cutouts 74 can extend through body 70 and open into lumen 72, in an example, or cutouts 74 can extend only partway through body 70. In the latter case, cutouts 74 can define a floor surface that separates lumen 72 from cutouts 74. In an example, two cutouts 74 can be provided, which are separated by a solid section 76 of body 70. Cutouts 74 can be defined by first and second flanges 75, 77 that are separated by a distance that is equal to or slightly greater than a thickness of arms 154 of horseshoe 150, described more fully below. A proximal face of jig nose 60 can also include one or more recesses 78, and by way of example two recesses 78 are shown in FIG. 2B.

Figure 3:
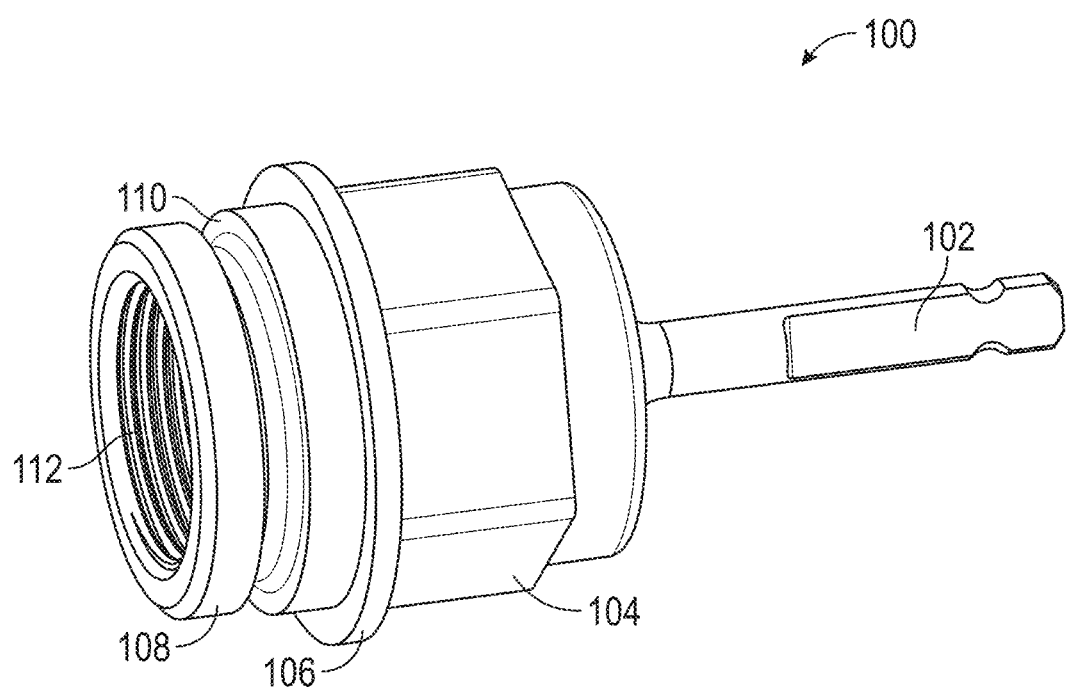
FIG. 3 is a side perspective view of a compression nut of the compression instrument shown in FIG. 1.

FIG. 3 is a perspective view of a compression nut 100 of compression instrument 90. Compression nut 90 can have a shaft 102 and a body 104. Shaft 102, in an example, can have a section shaped to engage with a mating portion of a driving tool, such as a female portion or socket of a T-handle or a straight handle. Thus, compression nut 100 can be rotated by a driving tool (not shown) that non-rotationally engages shaft 102.

A portion of body 104 of compression nut 100 can also be polygonal-shaped, in an example hexagonally shaped. An outer flange 106 can extend from body 104, and next to outer flange 106 can be a projection 108 that can be, in an example, cylindrically shaped. A groove 110 can extend into projection 108 about part or all of its circumference. Further, compression nut 100 can have a hollow threaded bore 112 that is internally threaded.

Figure 4:
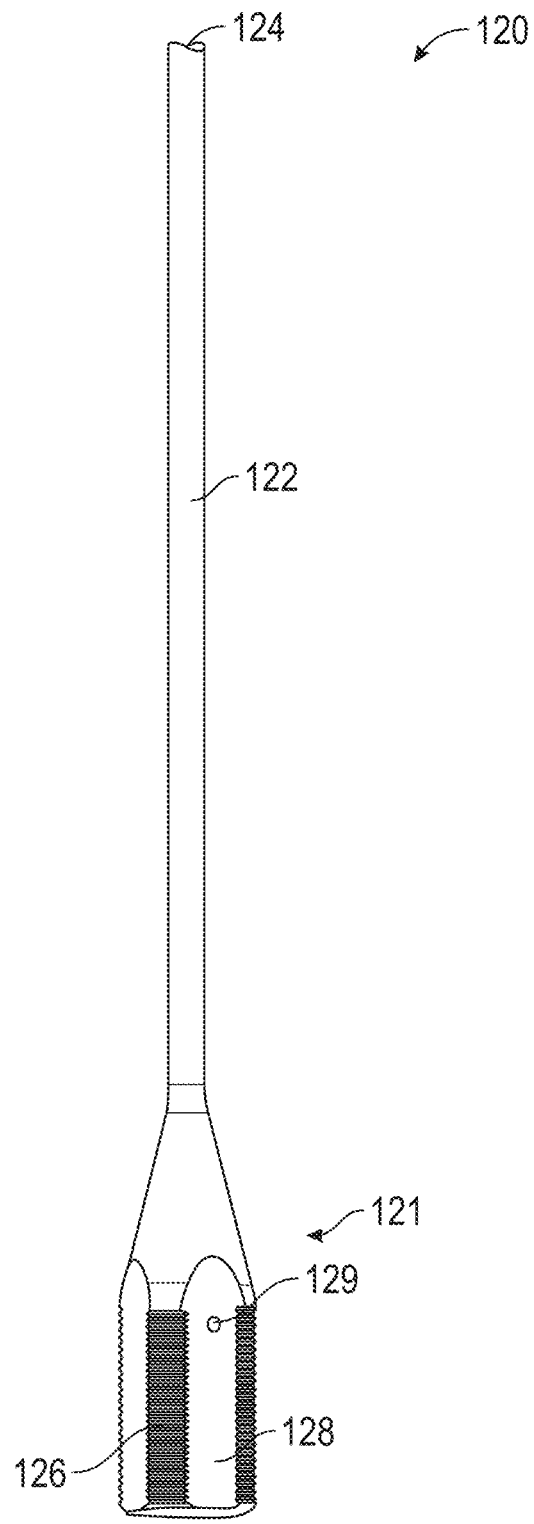
FIG. 4 is a side perspective view of a compression post of the compression instrument shown in FIG. 1.

Referring to FIGS. 1 and 4, a compression post 120 of compression instrument 90 is shown. Compression post 120 can include a shaft 122 and a threaded body 121 that can be received in threaded bore 112 of compression nut 100. Body 121 can have threaded sections 126 and substantially flat sections 128 arranged about its circumference. In an example, four curved or flat threaded sections 126 can be defined around body 121's circumference that, collectively, define a somewhat cylindrically-threaded shape. A distance between diametrically-opposite threaded sections 126 can be approximately equal to the inner diameter of hollow threaded bore 112 of compression nut 100. More or fewer threaded sections 126 can be included on body 121. Likewise, in an example, four substantially flat sections 128 can be included on body 121. Flat sections 128 can collectively define a polygonal-shape, in an example a somewhat square or rectangular shape. A distance between diametrically-opposite flat sections 128 can be approximately equal to the diameter of bore 146 of anti-rotation frame 130, discussed below. More or fewer flat sections 128 can be included on body 121. A distal end of shaft 122 of compression post 120 can also be curved as at 124 or otherwise shaped so that distal end 124 can engage with the shaft of a bone screw for compression purposes. In an example, distal end 124 can form a partially circular or hemi-circular shape, distal end 124 can be concave, or distal end 124 can be concave in perpendicular directions. Compression post 120 can also have one or more openings 129, and in an example a pair of openings 129, for receiving a pin(s) 137 (see e.g., FIG. 1).

Figure 5A:
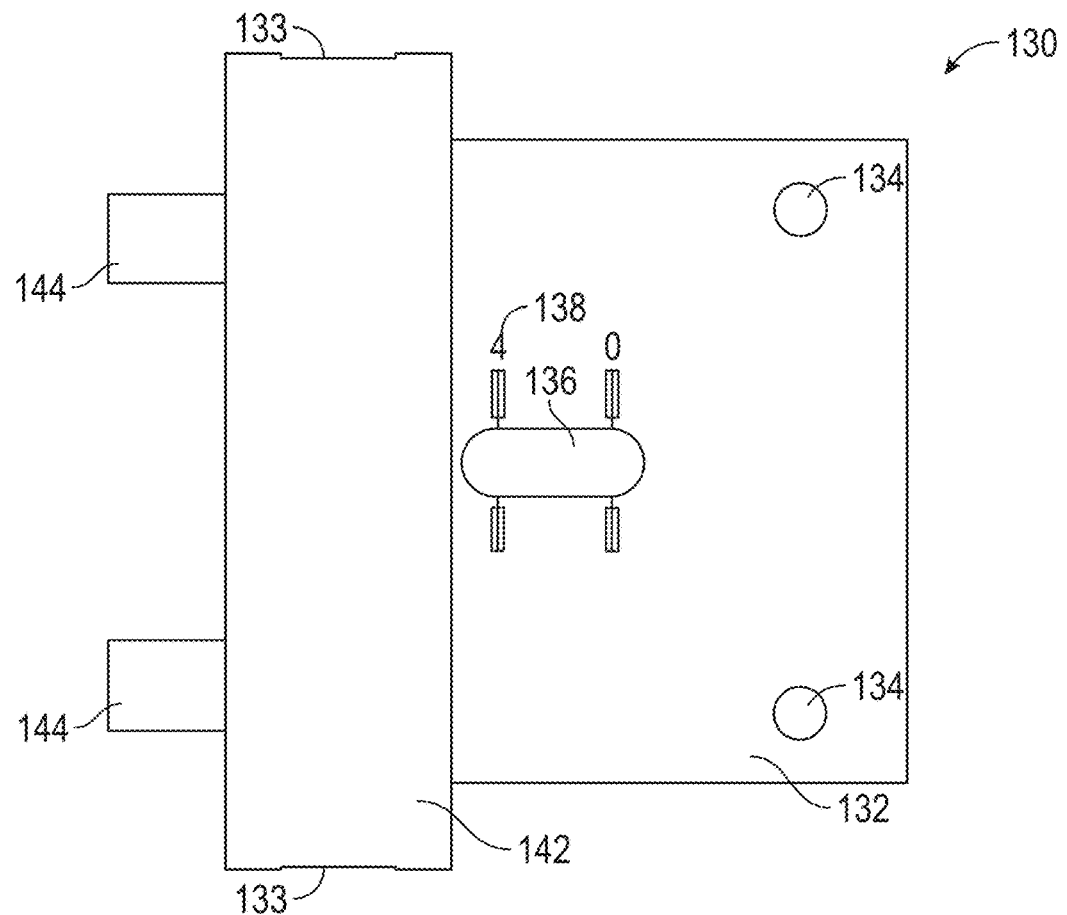
FIGS. 5A-B are side (FIG. 5A) and bottom (FIG. 5B) views of an anti-rotation frame of the compression instrument of FIG. 1.
Figure 5B:
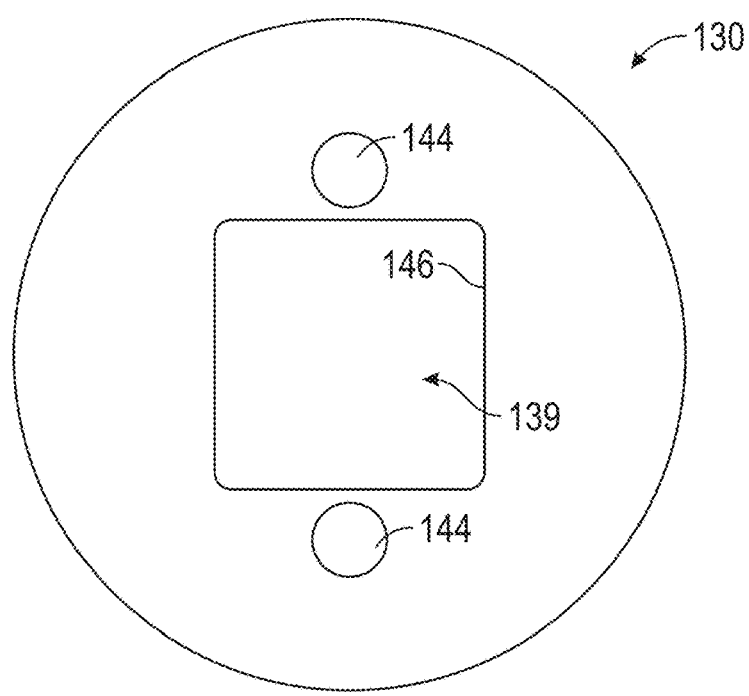
Figure 5C:
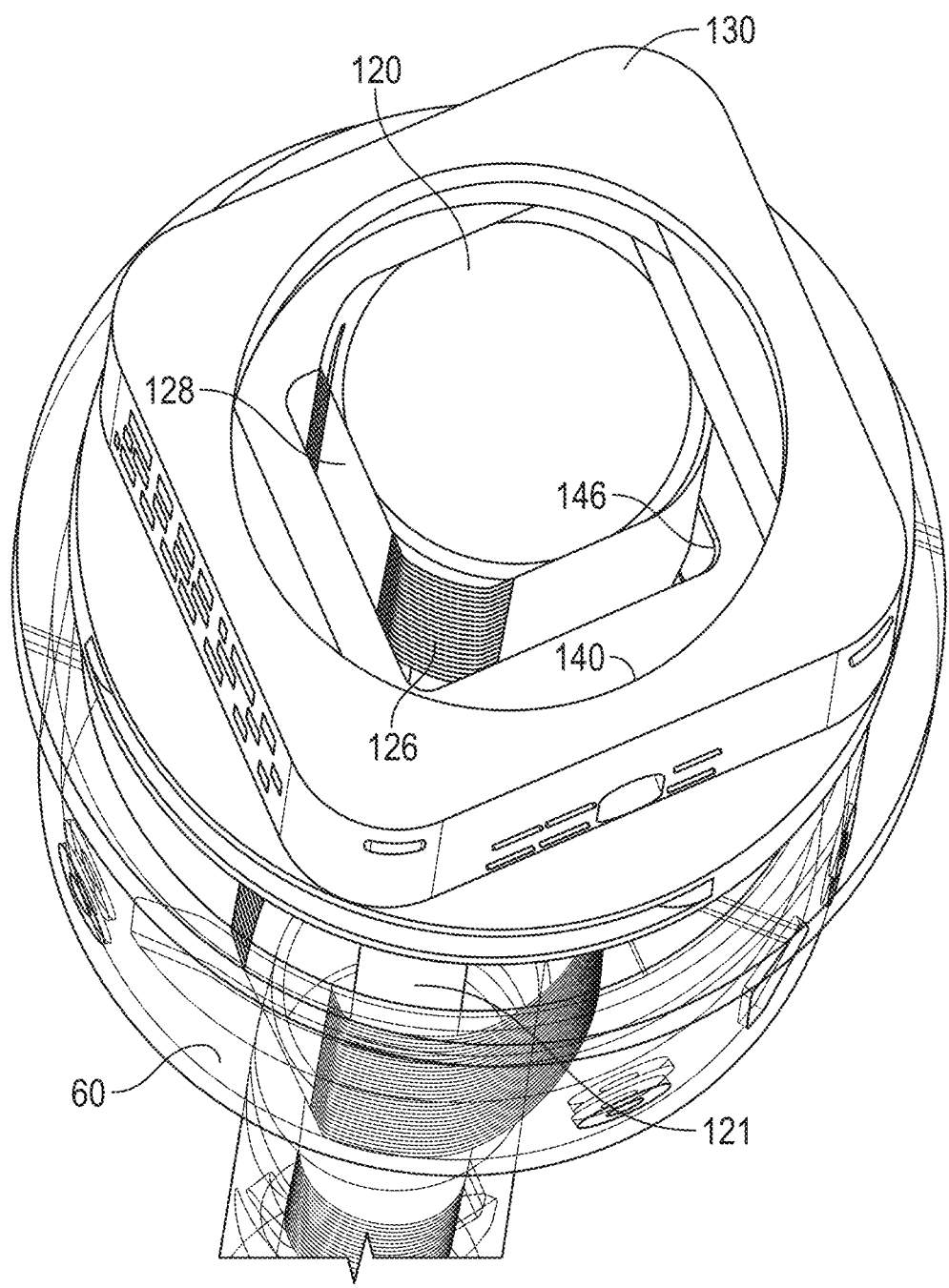
FIG. 5C is a top view of the anti-rotation frame of FIGS. 5A-B with a portion of the compression post of FIG. 4 extending through the frame.

Referring to FIGS. 5A-5C, an anti-rotation frame 130 is shown. Anti-rotation frame 130 can include a body 132 with a bore 139 that can define a first bore part 140 and a second bore part 146 (see e.g., FIGS. 5B-C). In an example, first bore part 140 can be cylindrical in shape, while second bore part 146 can be polygonal in shape, and in a specific example, square or rectangular. Second bore part 146 can alternatively take any non-rotational shape, such as oval, rounded with lobes, keyed, triangular, etc. First bore part 140 can have a diameter that is about equal to or alternatively slightly greater than an outer diameter of projection 108 of compression nut 100, and second bore part 146 can have an opening dimension or effective diameter that is equal to or alternatively slightly greater than a cross-sectional dimension or an effective diameter of body 121 of compression post 120, taken at flat sections 128.

Anti-rotation frame 130 can further include one or more openings 134, and in an example a pair of openings 134, which can extend through body 132 into first bore part 140. Openings 134 can receive pins 135, as shown in FIG. 1. In addition, body 132 can include one or more slots 136, and in an example a pair of slots 136, and distance gauge markings 138. Slot(s) 136 can be sized to receive a pin 137, as shown in FIG. 1.

A flange 142 can extend outwards from body 132 of anti-rotation frame 130 and define an outer diameter that is larger than the diameter of lumen 72 through jig nose 60. A set of posts 144 can also extend from flange 142 or body 132 and engage with recesses 78 of jig nose 60. Flange 142 can further include features to engage with a horseshoe 150 (see e.g., FIGS. 6A-B). In an example, flange 142 can have one or more slots, cutouts, or channels 133, in an example a pair of channels 133, for engaging with part of horseshoe 150.

FIG. 5C illustrates anti-rotation frame 130 attached to jig nose 60 with compression post 120 therein, but with compression nut 100 removed so as to be able to view internally inside compression instrument 90. FIG. 5C therefore illustrates how second bore part 146, in an example with a polygon shape, can engage with substantially flat sections 128 of body 121 so that compression post 120 is substantially rotationally fixed relative to anti-rotation frame 130. In particular, in an example substantially flat walls of second bore part 146 of anti-rotation frame 130 can engage with substantially flat sections 128 of compression post 120. Further, although not shown, compression nut 100 can be threaded onto body 121 of compression post 120 via its threaded internal bore 112 and can rotate within first bore part 140 of anti-rotation frame 130. In an example, pins 135 can extend through openings 134 in anti-rotation frame 130 and engage with groove 110 of compression nut 100 so that compression nut 100 can rotate in first bore part 140 of anti-rotation frame 130 and remain substantially fixed longitudinally relative to anti-rotation frame 130 as compression nut 100 is rotated.

Figure 6A:
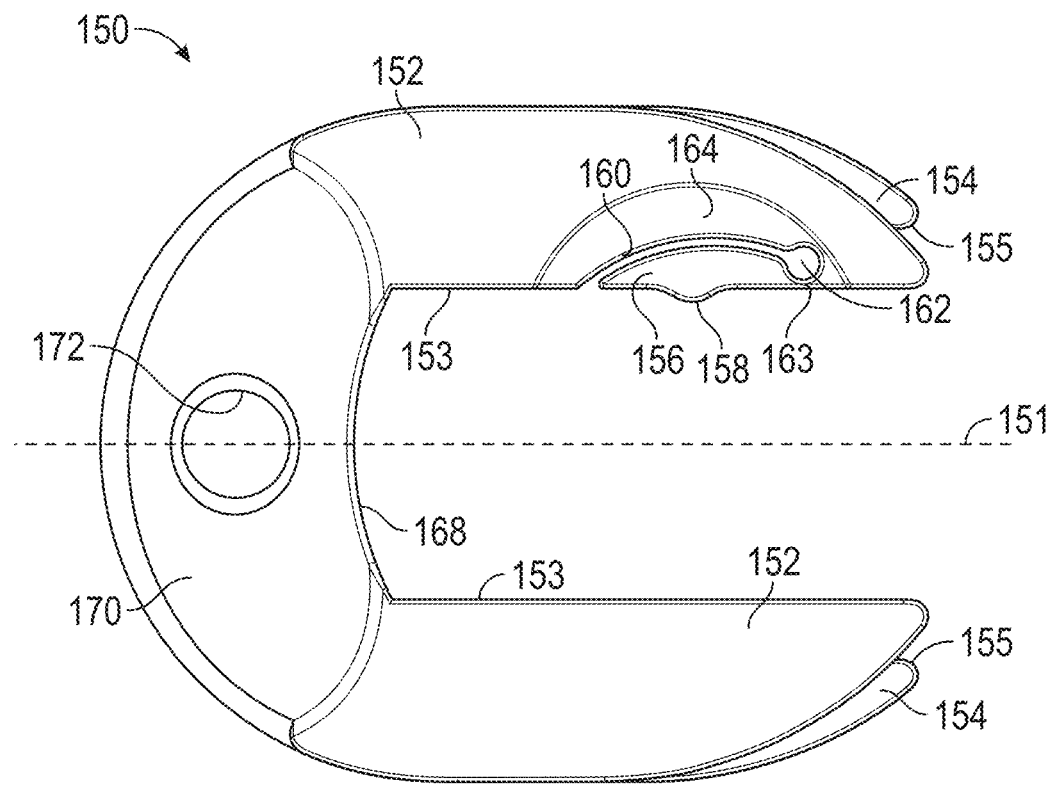
FIGS. 6A-B are top (FIG. 6A) and cross-sectional (FIG. 6B) views of a horseshoe usable with the compression instrument of FIG. 1.
Figure 6B:
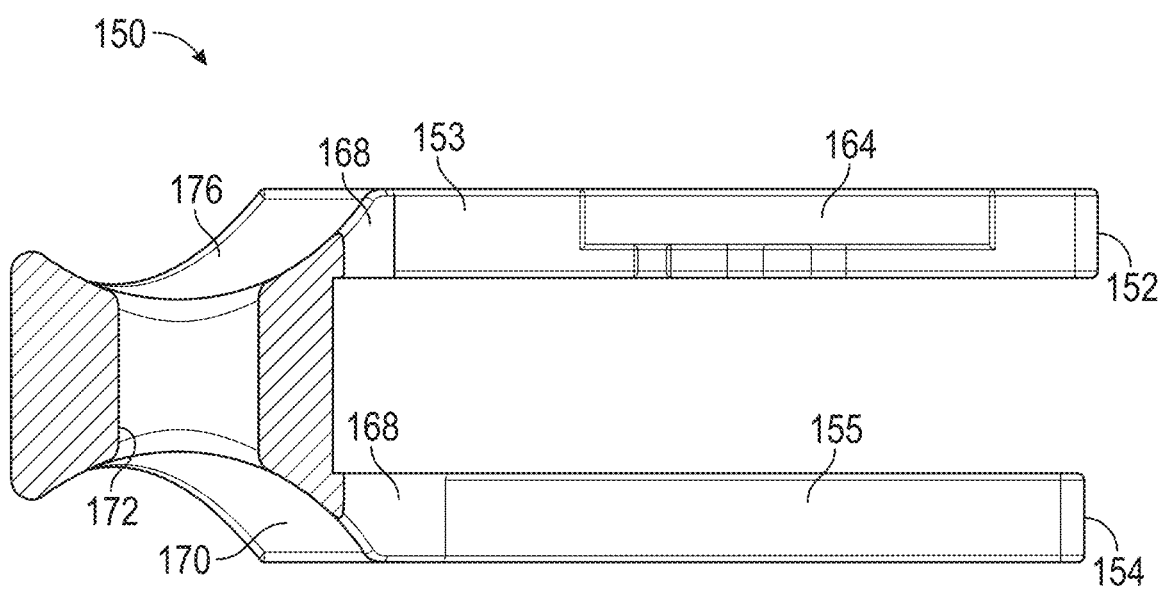

A horseshoe 150 is shown in FIGS. 6A-B. Horseshoe 150 can be used to connect jig nose 60 and anti-rotation frame 130 together during use of compression instrument 90. Horseshoe 150 can include a first set of arms 152 and a second set of arms 154. First set of arms 152 can be arranged to engage with anti-rotation frame 130, while second set of arms 154 can be arranged to engage with jig nose 60. An inside edge 153 of first set of arms 152 can extend closer to an axis 151 bifurcating horseshoe 150 as compared to an inside edge 155 of second set of arms 154. In other words, a distance between axis 151 and inside edge 153 of first set of arms 152 can be shorter than a distance between axis 151 and inside edge 155 of second set of arms 154. In an example, inside edges 153, 155 can run substantially parallel to axis 151, although in alternative examples inside edges 153, 155 can be angled relative to axis 151 (e.g., towards or away from axis 151).

Inside edge 153 of one of first set of arms 152 can further include a deflectable tab 156 having a protrusion 158. A slot 160 extending to a round opening 162 at an end of slot 160 can extend between deflectable tab 156 and the remainder of arm 152. Slot 160 and round opening 162 can be dimensioned so that a thin piece of material 163 joins deflectable tab 156 to arm 152 and allows deflectable tab 156 to resiliently deform inwards or outwards away from and towards axis 151. Protrusion 158 can define a portion of inside edge 153 of arm 152 that extends somewhat closer to axis 151 than a remainder of inside edge 153. Deflectable tab 156, slot 160, and opening 162 can be formed in a cutout 164 that is recessed in a portion of arm 152.

Each set of arms 152, 154 can also define a stop surface 168 that, in an example, can connect arms 152, 154. Stop surface 168 can prevent over-insertion of horseshoe 150. Horseshoe 150 can further include a finger-grasping part 170 that, in an example, is domed or curved in a first direction along axis 151 and in a second direction substantially perpendicular to axis 151. An opening or bore 172 can also extend through finger-grasping part 170.

Figure 7:
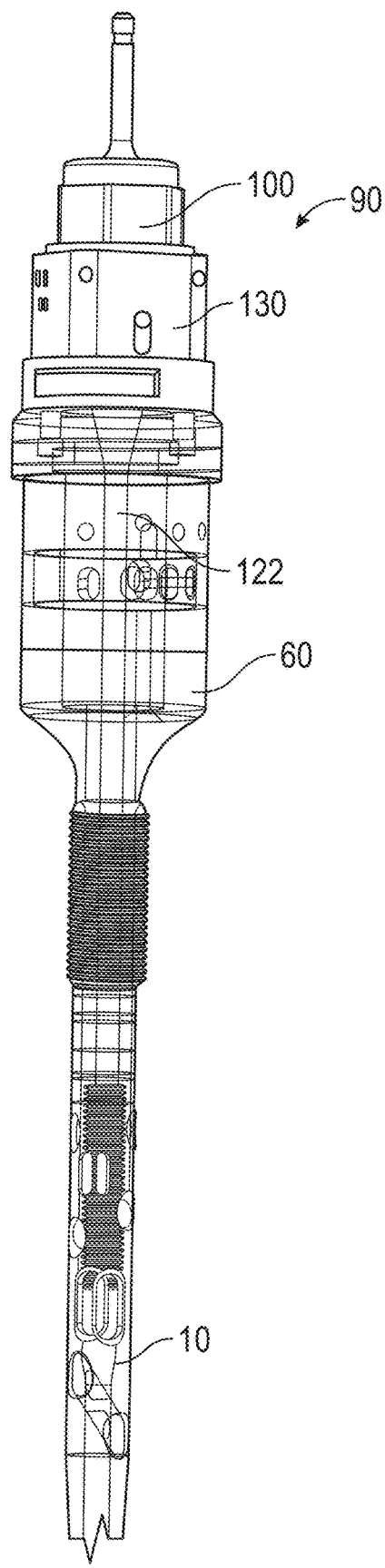
FIG. 7 is a partially-transparent view of the compression instrument of FIG. 1 attached to the intramedullary implant of FIG. 1.

FIG. 7 shows a semi-transparent view of compression instrument 90 attached to jig nose 60 and implant 10. Referring to FIGS. 1 and 7, compression instrument 90 can first be assembled by inserting compression post 120 into anti-rotation frame 130 so that body 121 of compression post 120 is situated within first and second bore parts 140, 146. In this way, substantially-flat sections 128 of body 121 of compression post 120 can contact the walls of second bore part 146, which in an example can be polygon-shaped. Curved threaded sections 126 can be rotatably disposed within first bore part 140, which in an example is cylindrically-shaped. A pin(s) 137 can then be inserted into opening(s) 129 in body 121 of compression post 120 and be positioned to ride in slot(s) 134 of anti-rotation frame 130. Subsequently, cylindrical projection 108 of compression nut 100 can be inserted into cylindrical first bore part 140 of anti-rotation frame 130 around body 121 of compression post 120. In this way, internal-threaded bore 112 of compression nut 100 can contact threaded sections 126 of compression post 120 and compression nut 100 can be rotatable relative to anti-rotation frame 130 within first bore part 140. Lastly, a pin(s) 135 can be inserted in opening(s) 134 of anti-rotation frame 130 and be received in groove 110 in projection 108 so that compression nut 100 can be rotated relative to anti-rotation frame 130 without moving longitudinally relative thereto.

As assembled, compression instrument 90 can then connect with jig nose 60 by inserting compression post 120 through lumen 72 of jig nose 60 and engaging posts 144 of anti-rotation frame 130 with recesses 78 of jig nose 60. Likewise, jig nose 60 can be connected to implant 10 by contacting protrusions 64 of jig nose 60 with cutouts or recesses 39 of implant 10. In other examples, a positive lock, both rotationally and longitudinally, can be established between jig nose 60 and implant 10 as, for instance, can occur with a threaded connection, a press-fit connection, a bayonet connection, or any other rotationally and longitudinally-locked connection. In these and other examples, the locked or unlocked connection between jig nose 60 and implant 10 can be releasable.

A method of using compression instrument 90 to achieve internal compression through implant 10 will now be disclosed. The method will be described with reference to implant 10 being an ankle arthrodesis nail. It is contemplated that implant 10 can be any intramedullary implant, however, used in other areas of the body. For instance, implant 10 can be a femoral intramedullary nail, a humeral intramedullary nail, a tibial intramedullary nail, or any other intramedullary nail used in other long bones of the body. Use in the tibia for ankle fusion is only one exemplary indication, which is described below for convenience.

First, a surgeon can make an incision in a patient's foot, for example the plantar aspect of a patient's foot, and prep the various bones to receive implant 10. This can involve drilling a pilot hole and/or reaming out a bore of a sufficient size to receive implant 10. The reamed bore can extend through the patient's calcaneus 46, talus 44, and into tibia 40 a sufficient distance for implant 10 to reside in the bore. The surgeon can then insert implant 10 into the bore so that implant 10 resides in the medullary canal of one or more bones, such as tibia 40. An example of implant 10 finally inserted into calcaneus 46, talus 44, and tibia 40 and secured thereto with various bone screws is shown in FIGS. 9A-C.

With implant 10 inserted into calcaneus 46, talus 44, and tibia 40, a bone screw 54 can be inserted into talus 44 through slot 24 of implant 10. One or more screws 52 can then be inserted through openings 14, 16, 18, 20 of implant 10 and into tibia 40. At this point, a CoreLock™ device is either inserted into or is predisposed within implant 10, and can be translated using suitable instrumentation to cause translation of screw 54 from a first proximal position in slot 24 to second position that is distal of the first position. Such translation can be anywhere between about two millimeters to about ten millimeters (2-10 mm), and in a specific example four millimeters (4 mm), and can cause compression of the tibio-talar joint.

More specifically, as mentioned above, a suitable CoreLock™ mechanism described in detail in the '031 Patent can be inserted or predisposed in implant 10 and used to cause translation of screw 54 in slot 24 using the corresponding instrumentation set forth in the '031 Patent, Merely as an example, a compression device 1024 (see FIGS. 45-45A) of the '031 Patent could be disposed within implant 10 and be aligned with slot 24. Second component 1076 of compression device 1024, in particular end opening 1084 thereof, can align with slot 24 so that screw 54 can be inserted through slot 24 and end opening 1084. Then, suitable instrumentation from the '031 Patent can be inserted into implant 10 to engage and rotate threaded first component 1046 of compression device 1024 against threading 34 of bore 32 of implant 10. In an example, such instrumentation can include a compression driver 1130 of the '031 Patent. In a further example, compression driver 1130 might have a component that engages with jig nose 60 and/or a shaft that can be inserted through jig nose 60 and into implant 10 to engage and rotate first component 1046 of compression device 1024. Such rotation of first component 1046, as described previously, can cause compression device 1024 to move distally within slot 24 from its proximal position to a distal position and cause compression of the tibio-talar joint. Formations 1090 on compression device 1024 can, in the process, engage bone screw 54 and lock bone screw within slot 24 once bone screw 54 has reached its distal-most position or until maximum compression of the tibio-talar joint is achieved. In its final position, in an example, bone screw 54 can extend medially about fifty degrees (50°) relative to sagittal plane 41.

A bone screw 56 can then be inserted into calcaneus 46 through slot 28 of implant 10. At this stage, compression instrument 90 can be used to internally compress and translate bone screw 56 from a first proximal position in slot 28 to a second position in slot 28 distal of the first position. In an example, such translation can be anywhere between about two millimeters to about ten millimeters (2-10 mm), in a specific example four millimeters (4 mm). In an example, first jig nose 60 can be attached to implant 10 by inserting protrusions 64 of jig nose 60 into recesses 39 of implant 10. In some examples, jig nose 60 can be positively locked rotationally and longitudinally to implant 10 through any number of means, including threading, press-fitting, or other connection mechanisms. With jig nose 60 attached to implant 10, shaft 122 of compression post 120 of compression instrument 90 can be inserted into and through lumen 72 of jig nose 60 until anti-rotation frame 130 contacts jig nose 60. In an example, posts 144 of anti-rotation frame 130 can be inserted into recesses 78 in jig nose 60 and flange 142 can be arranged to rest on the surfaces of jig nose 60 surrounding its bore 72.

Horseshoe 150 can then be applied to jig nose 60 and anti-rotation frame 130 to keep such components from separating as compression is applied in implant 10. In an example, referring to the cross-sectional view in FIG. 8, both sets of arms 152, 154 can be slid around jig nose 60 and anti-rotation frame 130. For instance, first set of arms 152 can be positioned within cutouts or slots 133 in anti-rotation frame 130, and second set of arms 154 can be positioned within cutouts or slots 74 in jig nose 60. In further example, a recess (not shown) can be present on a wall of cutouts 133 in anti-rotation frame 130 to interact with deflectable tab 156 of arm 152. Thus, as arms 152 are inserted into cutouts 133 of anti-rotation frame 130, a wall of one of cutouts 133 can engage protrusion 158 of deflectable tab 156 and cause it to deflect inwardly in a direction away from axis 151. Then, when protrusion 158 reaches the aforementioned recess (not shown), deflectable tab 156 can resiliently deflect back in a direction towards axis 151 and become housed in the recess. A surgeon can therefore be provided with tactile and/or auditory feedback in the form of a click that horseshoe 150 has engaged fully. Once horseshoe 150 is disposed on jig nose 60 and anti-rotation frame 150, arms 152, 154 can prevent jig nose 60 and anti-rotation frame 150 from separating as arms 152, 154 contact cutouts 133, 74.

Figure 8:
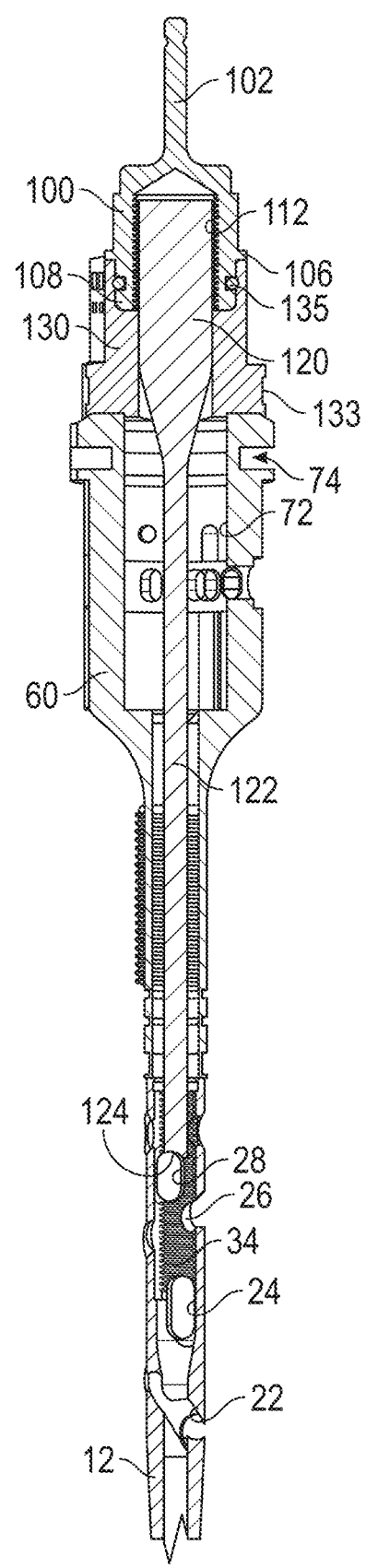
FIG. 8 is a cross-sectional view of FIG. 7.

Still referring to FIG. 8, a T-handle or other driving instrument (not shown) can then be attached to shaft 102 of compression nut 100 and rotated to cause rotation of compression nut 100. At the same time, curved end 124 of compression post 120 can be arranged next to screw 56 within slot 28. As compression nut 100 is rotated, its internal threaded bore 112 can engage with threaded sections 126 of compression post 120. Further, second bore part 146, which can be polygon-shaped, can contact substantially-flat sections 128 of compression post 120 and retain compression post 120 in a rotationally locked position relative to anti-rotation frame 130. As such, rotation of compression nut 100 can cause longitudinal translation of compression post 120 without corresponding rotation of compression post 120 due to ant-rotation frame 130. In addition, compression nut 100 can be retained longitudinally relative to anti-rotation frame 130 by virtue of pin(s) 135 riding in groove 110 of projection 108 of compression nut 100. Pin(s) 137 can also ride in slot 136 of anti-rotation frame 130 to determine the amount of movement of compression post 120. In an example, distance gauge markings 138, which can designate zero millimeters (0 mm) of movement and four millimeters (4 mm) of movement, can show the amount of movement of compression post 120 since such pin(s) 137 can ride in slot 136 as post 120 is moved distally.

Compression nut 100 can be rotated to move compression post 120 distally and cause curved distal end 124 to contact screw 56 and move screw 56, internally within implant 10, from a first proximal position in slot 28 to a second position distal of the first position. Such movement of screw 56 can cause compression of the calcaneus-talar joint, as shown in FIG. 9A. Thus, the present implant 10 and compression instrument 90 can allow for two-stage internal compression within implant 10 to cause compression of the tibio-talar joint and the calcaneus-talar joint. Such internal compression can reduce problems commonly experienced with other compression techniques, such as bone float and misalignment. Internal compression can also avoid some issues that might be experienced with external compression, such as patient trauma. In the final position, screw 56 can extend through calcaneus 46 roughly medial-to-lateral (e.g., substantially perpendicular to sagittal axis 41), as shown in FIG. 9C.

Screw 55 can then be inserted into calcaneus 46, through angled opening 26 in implant 10, and into talus 44 across the subtalar joint (calcaneus-talar joint). Screw 55 can therefore fix the subtalar compression affected using the above method. Compression instrument 90 can then be removed from implant 10 as screw 55 maintains the subtalar compression. In a particular example, compression nut 100 can be rotated to cause compression post 120 to retract out of contact with screw 56 once screw 55 is inserted across the subtalar joint. Then, horseshoe 150 can be removed and compression instrument 90 removed from connection with implant 10. In the final position, screw 55 can extend twenty-five degrees (25°) superiorly relative to a transverse ankle plane and thirteen degrees (13°) medially relative to sagittal plane 41.

Subsequently, screw 57 can be inserted into calcaneus 46 and through angled opening 30 in implant 10. In addition, screw 53 can extend into tibia 40, through angled opening 22, and into talus 44 across the tibio-talar joint. In an example, screw 53 can also extend into navicular 49 across the talar-navicular joint. In the final position, screw 57 can extend five degrees (5°) superiorly relative to a transverse ankle plane and five degrees (5°) laterally relative to sagittal plane 41. Likewise, in its final position, screw 53 can extend forty-five degrees (45°) inferiorly relative to a transverse ankle plane and twenty-eight degrees (28°) medially relative to sagittal plane 41.

With the above construct, the tibio-talar joint and the subtalar joint can be compressed internally in two-stages, and various screws can be used along with implant 10 to fix the compression and the ankle joint (e.g., for ankle fusion to occur). Suitable bone graft material or other augments can be used to assist with the fusion.

In the devices shown in the figures, particular structures are shown as being adapted for use in an internal compression method. The invention(s) also contemplates the use of any alternative structures for such purposes, including structures having different lengths, shapes, and/or configurations. For example, it is contemplated that any of openings 14, 16, 18, 20 can be threaded or unthreaded to engage with bone screws 52 and, likewise, any of angled openings 22, 26, 30 in any combination can be threaded or unthreaded to engage with the relevant bone screws. Further, it is to be appreciated that, although not discussed above, a CoreLock™ device can be used with angled openings 22, 26, 30 to lock an associated bone screw in any of openings 22, 26, 30. Such CoreLock™ devices are described in detail in the '031 and '590 Patents.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. An implant system comprising:
   an intramedullary implant, the intramedullary implant comprising:
   a jig nose;
   an elongate shaft sized and shaped to be implanted in an intramedullary canal of a tibia of a patient, the elongate shaft configured to attach to the jig nose and having an internal bore;
   a first angled opening through the shaft, the first angled opening configured to define a first axis that extends through the tibia and into a talus bone of the patient across a tibio-talar joint when the intramedullary implant is implanted;
   a first slot extending through the shaft, the first slot configured to define a second axis that extends into the patient's talus when the intramedullary implant is implanted, the first slot being configured to allow a first fixation member to translate axially relative to the shaft within the first slot from a first position to a second different position to compress a tibio-talar joint;
   a second elongate slot through the shaft, the second elongate slot configured to define a third axis that extends into the patient's calcaneus when the intramedullary implant is implanted; and
   a second angled opening through the shaft, the second angled opening configured to define a fourth axis that extends into a calcaneus bone of the patient when the intramedullary implant is implanted;
   a first fixation member having a shaft;
   a second fixation member having a shaft, wherein the second elongate slot is configured to allow a second fixation member to translate axially relative to the shaft within the second slot from a first position to a second different position to compress a subtalar joint;

a telescoping clamp attachable to the jig nose and having a body configured to insert into the internal bore of the elongate shaft, wherein the body of the telescoping clamp defines a first area shaped to engage the shaft of the first fixation member, wherein the telescoping clamp is disposable in the internal bore of the implant adjacent the first slot and is movable within the internal bore, with the first fixation member in the first slot, so that the first area of the body of the telescoping clamp engages the shaft of the first fixation member and moves the first fixation member from a first position in the first slot to a second different position;

a compression instrument attachable to the jig nose upon removal of the telescoping clamp and having a shaft configured to insert into the internal bore of the elongate shaft, wherein the shaft of the compression instrument has a first section shaped to engage the shaft of the second fixation member, wherein the shaft of the compression instrument is movable within the internal bore of the elongate shaft, with the second fixation member in the second slot, so that the first section of the shaft engages the shaft of the second fixation member and moves the second fixation member from a first position in the second slot to a second different position; and an anti-rotation member attachable to the jig nose and configured to be disposed about the shaft of the compression instrument and configured to rotationally lock the shaft of the compression instrument relative to the anti-rotation member.

2. The implant system of claim 1, wherein the shaft of the compression instrument has a threaded body, the compression instrument further comprising a threaded nut rotatably engaged to the threaded body.

3. The implant system of claim 2, wherein rotation of the threaded nut relative to the threaded body causes the shaft of the compression instrument to move longitudinally relative to the threaded nut from a first position to a second different position.

4. The implant system of claim 3, wherein rotation of the threaded nut relative to the threaded body causes the shaft of the compression instrument to move longitudinally, but not rotationally.

5. The implant system of claim 1, wherein the telescoping clamp comprises a threaded portion that is rotatable relative to the body, and the internal bore of the implant is threaded, such that rotation of the threaded portion of the telescoping clamp relative to the body within the threaded internal bore causes the telescoping clamp to move from a first position to a second position within the threaded internal bore.

6. The implant system of claim 1, wherein the jig nose has a shaft and a body and an internal bore through the shaft and the body, wherein a portion of the jig nose is engageable with the intramedullary implant, and the shaft of the compression instrument is insertable into the internal bore of the jig nose.

7. The implant system of claim 1, wherein the internal bore is threaded.

8. Then implant system of claim 1, further comprising third, and fourth fixation members each defining a diameter, wherein the first and second slots each has a length that is anywhere between about 125-500% of the diameter of the second and third fixation members, and a width that is equal to or under 120% of the diameter of the second and third fixation members, respectively.

9. The implant system of claim 1, further comprising a third angled opening through the shaft, the third angled opening configured to define a fifth axis that extends through the calcaneus and into a talus bone of the patient across the subtalar joint when the intramedullary implant is implanted.

10. An implant system comprising:
an intramedullary implant comprising:
a jig nose having a shaft and a body and an internal bore through the shaft and the body;
a shaft sized and shaped to be implanted in an intramedullary canal of a tibia of a patient, the shaft configured to attach to the jig nose and having an internal bore;
a first slot extending through the shaft, the first slot configured to define a first axis that extends into the patient's talus when the intramedullary implant is implanted, the first slot being configured to allow a first fixation member to translate axially relative to the shaft within the first slot from a first position to a second different position to compress a tibio-talar joint;
a second elongate slot through the shaft, the second elongate slot configured to define a second axis that extends into the patient's calcaneus when the intramedullary implant is implanted, the second elongate slot being configured to allow a second fixation member to translate axially relative to the shaft within the second slot from a first position to a second different position to compress a subtalar joint;
a first fixation member having a shaft;
a second fixation member having a shaft;
a third fixation member having a shaft;
a telescoping clamp attachable to the jig nose and having a body configured to insert into the internal bore of the elongate shaft, wherein the body of the telescoping clamp defines a first area, shaped to engage the shaft of the first fixation member, wherein the telescoping clamp is disposable in the internal bore of the implant adjacent the first slot and is movable within the internal bore, with the first fixation member in the first slot, so that the first area of the body of the telescoping clamp engages the shaft of the first fixation member and moves the first fixation member from a first position in the first slot to a second different position;
a compression instrument attachable to the jig nose upon removal of the telescoping clamp and having a shaft configured to insert into the internal bore of the elongate shaft, wherein the shaft of the compression instrument has a first section shaped to engage the shaft of the second fixation member, wherein the shaft of the compression instrument is movable within the internal bore of the elongate shaft, with the second fixation member in the second slot, so that the first section of the shaft engages the shaft of the second fixation member and moves the second fixation member from a first position in the second slot to a second different position; and
an anti-rotation member attachable to the jig nose and configured to be disposed about the shaft of the compression instrument and configured to rotationally lock the shaft of the compression instrument relative to the anti-rotation member.

11. The implant system of claim 10, wherein the intramedullary implant further comprises:
a first angled opening through the shaft of the intramedullary implant, the first angled opening configured to define a third axis that extends through the tibia and into a talus bone of the patient across a tibio-talar joint when the intramedullary implant is implanted; and a second angled opening through the shaft of the intramedullary implant, the second angled opening configured to define a fourth axis that extends into a calcaneus bone of the patient when the intramedullary implant is implanted.

12. The implant system of claim 11, further comprising a third angled opening through the shaft of the intramedullary implant, the third angled opening configured to define a fifth axis that extends through the calcaneus and into a talus bone of the patient across the subtalar joint when the intramedullary implant is implanted.

13. An implant system comprising:
an intramedullary implant comprising:
a shaft sized and shaped to be implanted in an intramedullary canal of a tibia of a patient, the shaft having an internal bore;
a first slot extending through the shaft, the first slot configured to define a first axis that extends into the patient's talus when the intramedullary implant is implanted, the first slot being configured to allow a first fixation member to translate axially relative to the shaft within the first slot from a first position to a second different position to compress a tibio-talar joint; and
a second elongate slot through the shaft, the second elongate slot configured to define a second axis that extends into the patient's calcaneus when the intramedullary implant is implanted, the second elongate slot being configured to allow a second fixation member to translate axially relative to the shaft within the second slot from a first position to a second different position to compress a subtalar joint;
a first fixation member having a shaft;
a second fixation member having a shaft;
a third fixation member having a shaft; and
a compression instrument having a shaft with a first section shaped to engage the shaft of the first fixation member, wherein the shaft of the compression instrument is movable within the internal bore of the implant, with the first fixation member in the first slot, so that the first section of the shaft engages the shaft of the first fixation member and moves the first fixation member from a first position in the first slot to a second different position, wherein the first and second slots each has a length that is anywhere between about 125-500% of the diameter of the second and third fixation members, and a width that is equal to or under 120% of the diameter of the second and third fixation members, respectively.

* * * * *

UNITED STATES PATENT AND TRADEMARK OFFICE
CERTIFICATE OF CORRECTION

PATENT NO. : 10,869,701 B2  
APPLICATION NO. : 15/851943  
DATED : December 22, 2020  
INVENTOR(S) : Van Dyke et al.

Page 1 of 1

It is certified that error appears in the above-identified patent and that said Letters Patent is hereby corrected as shown below:

In the Claims

In Column 16, Line 35, in Claim 10, delete "area," and insert --area-- therefor

Signed and Sealed this  
Second Day of March, 2021

Drew Hirshfeld  
*Performing the Functions and Duties of the*  
*Under Secretary of Commerce for Intellectual Property and*  
*Director of the United States Patent and Trademark Office*